(12) United States Patent
McGrath

(10) Patent No.: US 9,387,487 B2
(45) Date of Patent: Jul. 12, 2016

(54) EROSION-RESISTANT CONDUCTIVE COMPOSITE MATERIAL COLLECTING ELECTRODE FOR WESP

(75) Inventor: Paul McGrath, Mississauga (CA)

(73) Assignee: MEGTEC TurboSonic Inc., Waterloo, Ontario (CA)

( * ) Notice: Subject to any disclaimer, the term of this patent is extended or adjusted under 35 U.S.C. 154(b) by 0 days.

(21) Appl. No.: 14/007,666

(22) PCT Filed: Mar. 28, 2012

(86) PCT No.: PCT/CA2012/000277
§ 371 (c)(1),
(2), (4) Date: Feb. 19, 2014

(87) PCT Pub. No.: WO2012/129656
PCT Pub. Date: Oct. 4, 2012

(65) Prior Publication Data
US 2014/0150659 A1  Jun. 5, 2014

Related U.S. Application Data

(60) Provisional application No. 61/468,199, filed on Mar. 28, 2011.

(51) Int. Cl.
*B03C 3/53* (2006.01)
*B03C 3/16* (2006.01)
*B03C 3/41* (2006.01)
(Continued)

(52) U.S. Cl.
CPC ... *B03C 3/53* (2013.01); *B03C 3/16* (2013.01); *B03C 3/41* (2013.01); *B03C 3/49* (2013.01); *B03C 3/64* (2013.01); *A61L 9/16* (2013.01);
(Continued)

(58) Field of Classification Search
CPC ............. B03C 3/16; B03C 3/41; B03C 3/53; B03C 3/64
USPC ................... 96/36, 44, 66, 69, 99; 95/75–76; 422/249, 254, 268
See application file for complete search history.

(56) References Cited

U.S. PATENT DOCUMENTS 687,109 A  11/1901  Baum
710,655 A  10/1902  Angell
(Continued)

FOREIGN PATENT DOCUMENTS

CA  643389 A  6/1962
CA  2505248 A1  5/2004
(Continued)

OTHER PUBLICATIONS

Supplementary European Search Report for European Patent Application No. 12763929.2, dated Nov. 20, 2014.
(Continued)

*Primary Examiner* — Jason M Greene
*Assistant Examiner* — Karla Hawkins
(74) *Attorney, Agent, or Firm* — Sim & McBurney

(57) ABSTRACT

A collecting electrode for use in wet electrostatic precipitators, the collecting electrode being fabricated from an electrically-conductive, corrosion resistant and temperature and spark resistant composite material comprising carbon fiber and thermosetting resin so as to pro\ the collecting electrode with an improved arc resistance, as dictated by erosion density and direction, by controlling the weave pattern and/or fabric thickness of the carbon fibers.

4 Claims, 6 Drawing Sheets

(51) Int. Cl.
   *B03C 3/49* (2006.01)
   *B03C 3/64* (2006.01)
   *A61L 9/16* (2006.01)

(52) U.S. Cl.
   CPC ......... *B03C 2201/08* (2013.01); *B03C 2201/10* (2013.01)

(56) References Cited

U.S. PATENT DOCUMENTS

| | | | |
|---|---|---|---|
| 1,322,163 A | 11/1919 | Conover | |
| 1,399,422 A | 12/1921 | Chubb | |
| 1,602,597 A | 10/1926 | Staude | |
| 1,773,073 A | 8/1930 | Beach | |
| 1,773,973 A | 8/1930 | Edgar | |
| 1,793,664 A | 2/1931 | Anderson | |
| 1,813,637 A | 7/1931 | Powers | |
| 2,357,355 A | 9/1944 | Penney | |
| 2,567,709 A | 9/1951 | Hedberg | |
| 2,696,892 A | 12/1954 | Campbell | |
| 2,712,362 A | 7/1955 | Winklepleck | |
| 2,720,551 A | 10/1955 | Wastvind et al. | |
| 2,794,847 A | 6/1957 | Streuber et al. | |
| 2,806,896 A | 9/1957 | Streuber et al. | |
| 2,830,869 A | 4/1958 | Limerick | |
| 2,935,375 A | 5/1960 | Boucher | |
| 3,046,716 A | 7/1962 | Rodger | |
| 3,104,963 A | 9/1963 | Bonnett | |
| 3,297,903 A | 1/1967 | Riek | |
| 3,403,497 A | 10/1968 | Vander Mey | |
| 3,495,123 A | 2/1970 | Raddatz | |
| 3,512,340 A | 5/1970 | Golucke et al. | |
| 3,584,440 A | 6/1971 | Vigil | |
| 3,595,983 A | 7/1971 | Muller et al. | |
| 3,605,386 A | 9/1971 | Erwin et al. | |
| 3,716,966 A | 2/1973 | De Seversky | |
| 3,721,069 A | 3/1973 | Walker | |
| 3,745,751 A | 7/1973 | Zey et al. | |
| 3,765,154 A | 10/1973 | Hardt et al. | |
| 3,793,802 A | 2/1974 | Hardt | |
| 3,798,883 A | 3/1974 | Heeney | |
| 3,883,328 A | 5/1975 | Spain | |
| 3,918,939 A | 11/1975 | Hardt | |
| 4,070,424 A | 1/1978 | Olson et al. | |
| 4,117,255 A | 9/1978 | Kawaike et al. | |
| 4,141,698 A | 2/1979 | Kihlstedt et al. | |
| 4,155,792 A | 5/1979 | Gelhaar et al. | |
| 4,177,047 A | 12/1979 | Goland | |
| 4,247,307 A | 1/1981 | Chang | |
| 4,251,682 A | 2/1981 | Ebert et al. | |
| 4,290,738 A | 9/1981 | Liebert et al. | |
| 4,294,591 A | 10/1981 | Kahl | |
| 4,318,719 A | 3/1982 | Kato et al. | |
| 4,360,367 A | 11/1982 | Prior | |
| 4,375,364 A | 3/1983 | Van Hoesen et al. | |
| 4,431,617 A | 2/1984 | Farin | |
| 4,439,216 A | 3/1984 | Perryman | |
| 4,505,776 A | 3/1985 | Murray | |
| 4,507,341 A | 3/1985 | Heseltine | |
| 4,522,634 A | 6/1985 | Frank | |
| 4,601,731 A | 7/1986 | Michelson | |
| 4,704,363 A | 11/1987 | Ziegler | |
| 4,846,857 A | 7/1989 | Tachibana | |
| 4,885,139 A | 12/1989 | Sparks et al. | |
| 4,893,752 A | 1/1990 | Spink et al. | |
| 4,908,047 A | 3/1990 | Leonard | |
| 4,948,399 A | 8/1990 | Reuffurth et al. | |
| 4,957,512 A | 9/1990 | Denisov et al. | |
| 5,192,517 A | 3/1993 | Spink | |
| 5,248,324 A | 9/1993 | Hara | |
| 5,254,155 A | 10/1993 | Mensi | |
| 5,295,310 A | 3/1994 | Eriksson | |
| 5,308,589 A | 5/1994 | Yung | |
| 5,344,481 A | 9/1994 | Pettersson | |
| 5,363,567 A | 11/1994 | Best | |
| 5,364,457 A | 11/1994 | Cameron | |
| 5,395,430 A | 3/1995 | Lundgren et al. | |
| 5,401,302 A | 3/1995 | Schulmerich et al. | |
| 5,482,540 A | 1/1996 | Trinward et al. | |
| 5,498,462 A | 3/1996 | Darfler | |
| 5,599,508 A | 2/1997 | Martinelli et al. | |
| 5,603,751 A | 2/1997 | Ackerson | |
| 5,603,752 A | 2/1997 | Hara | |
| 5,714,226 A | 2/1998 | Disselbeck | |
| 5,843,210 A | 12/1998 | Paranjpe et al. | |
| 5,855,652 A | 1/1999 | Talley | |
| 5,917,138 A | 6/1999 | Taylor | |
| 5,922,290 A | 7/1999 | Jenne et al. | |
| 6,004,375 A | 12/1999 | Gutsch et al. | |
| 6,106,592 A * | 8/2000 | Paranjpe et al. | ........... 95/65 |
| 6,156,098 A | 12/2000 | Richards | |
| 6,176,902 B1 | 1/2001 | Matsubara | |
| 6,231,643 B1 * | 5/2001 | Pasic et al. | ........... 95/75 |
| 6,267,802 B1 | 7/2001 | Baldrey et al. | |
| 6,508,861 B1 | 1/2003 | Ray | |
| 6,579,349 B1 | 6/2003 | Ting et al. | |
| 6,579,506 B2 | 6/2003 | Spink et al. | |
| 6,599,349 B1 | 7/2003 | Scharkowski | |
| 6,620,224 B1 | 9/2003 | Sato | |
| 6,974,494 B1 | 12/2005 | Zahedi | |
| 7,160,348 B2 | 1/2007 | Allan | |
| 7,160,358 B2 | 1/2007 | Spink et al. | |
| 7,938,146 B2 | 5/2011 | Brooks et al. | |
| 8,597,416 B2 | 12/2013 | Allan | |
| 2002/0090873 A1 * | 7/2002 | Moody | ........ B32B 5/26 442/268 |
| 2003/0082315 A1 | 5/2003 | Mehlman et al. | |
| 2004/0139853 A1 | 7/2004 | Bologa et al. | |
| 2004/0169162 A1 | 9/2004 | Xiao et al. | |
| 2004/0221720 A1 | 11/2004 | Anderson et al. | |
| 2004/0226449 A1 | 11/2004 | Heckel et al. | |
| 2005/0028674 A1 | 2/2005 | Allan | |
| 2005/0045038 A1 | 3/2005 | Huang | |
| 2005/0123717 A1 | 6/2005 | Shen et al. | |
| 2005/0229780 A1 | 10/2005 | Spink et al. | |
| 2007/0051237 A1 | 3/2007 | Furukawa et al. | |
| 2007/0201183 A1 | 8/2007 | Komatsu et al. | |
| 2007/0283903 A1 | 12/2007 | Bologa et al. | |
| 2009/0014378 A1 | 1/2009 | Hundley et al. | |
| 2009/0142980 A1 | 6/2009 | Chen | |
| 2009/0241781 A1 | 10/2009 | Triscori et al. | |

FOREIGN PATENT DOCUMENTS

| | | |
|---|---|---|
| CN | 2376335 Y | 5/2000 |
| DE | 30 27 307 A1 | 5/1981 |
| DE | 102004001463 A1 | 8/2005 |
| GB | 553420 A | 5/1943 |
| GB | 556 939 A | 10/1943 |
| GB | 1413127 | 11/1975 |
| JP | 5335674 A | 11/1975 |
| JP | 52-1574 A | 1/1977 |
| JP | 57194001 | 11/1982 |
| JP | 60 149449 A | 8/1985 |
| JP | 1-258754 A | 10/1989 |
| JP | 06190300 A | 7/1994 |
| JP | 10202142 A | 4/1998 |
| JP | 11151410 | 6/1999 |
| WO | 9005027 A1 | 5/1990 |
| WO | 9219380 A1 | 11/1992 |
| WO | 9601678 A1 | 1/1996 |
| WO | 2005007295 A1 | 1/2005 |
| WO | 2005097297 A1 | 10/2005 |
| WO | 2006113749 | 10/2006 |
| WO | 2008154735 A1 | 12/2008 |
| WO | 2010108256 A1 | 9/2010 |
| WO | 2011/120137 A1 | 10/2011 |

OTHER PUBLICATIONS

Third Chinese Office Action, Jan. 14, 2015, CN Application No. 201080022796.0.
Written Opinion, Jan. 23, 2006, International Application No. PCT/CA2004/001037.

(56) References Cited

OTHER PUBLICATIONS

International Preliminary Report on Patentability, Jan. 23, 2006, International Application No. PCT/CA2004/001037.
Written Opinion, Aug. 12, 2005, International Application No. PCT/CA2005/000549.
International Preliminary Report on Patentability, Aug. 12, 2005, International Application No. PCT/CA2005/000549.
Communication pursuant to Article 94(3) EPC, Jul. 18, 2012, EP Application No. 04737969.8.
Communication pursuant to Article 94(3) EPC, Sep. 23, 2009, EP Application No. 04737969.8.
Written Opinion, May 1, 2006, International Application No. PCT/CA2006/000238.
International Preliminary Report on Patentability, Oct. 11, 2006, International Application No. PCT/CA2006/000238.
Written Opinion, Aug. 28, 2006, International Application No. PCT/CA2006/000755.
International Preliminary Report on Patentability, Nov. 13, 2007, International Application No. PCT/CA2006/000755.
Communication pursuant to Article 94(3) EPC, Apr. 23, 2014, EP Application No. 05735662.8.
Communication pursuant to Article 94(3) EPC, Sep. 15, 2011, EP Application No. 05735662.8.
EPC Examination, Mar. 10, 2009, EP Application No. 05735662.8.
Supplementary European Search Report, Jul. 12, 2007, EP Application No. 05735662.8.
Canadian Office Action, Sep. 9, 2010, Canadian Application No. 2562372.
Canadian Office Action, Jul. 30, 2012, Canadian Application No. 2598187.
Canadian Office Action, Jun. 14, 2013, Canadian Application No. 2598187.
Canadian Office Action, Feb. 6, 2014, Canadian Application No. 2598187.
Response to Communication, Aug. 26, 2014, EP Application No. 06705193.8.
Communication pursuant to Article 94(3) EPC, Apr. 17, 2014, EP Application No. 06705193.8.
Canadian Office Action, Feb. 24, 2012, Canadian Application No. 2607978.
Communication pursuant to Article 94(3) EPC, Dec. 4, 2012, EP Application No. 08741470.6.
Written Opinion, Jul. 21 2008, International Application No. PCT/CA2008/000752.
International Preliminary Report on Patentability, Jul. 21 2008, International Application No. PCT/CA2008/000752.
Written Opinion, Sep. 19, 2008, International Application No. PCT/CA2008/001157.
International Preliminary Report on Patentability, Sep. 19, 2008, International Application No. PCT/CA2008/001157.
Canadian Office Action, Mar. 12, 2014, Canadian Application No. 2684781.
Canadian Office Action, Oct. 2, 2014, Canadian Application No. 2684781.
EPC Examination, May 14, 2013, EP Application No. 08748166.9.
Written Opinion, May 31, 2010, International Application No. PCT/CA2010/000377.
International Preliminary Report on Patentability, May 31, 2010, International Application No. PCT/CA2010/000377.
Written Opinion, Dec. 22, 2010, International Application No. PCT/CA2010/001404.
International Preliminary Report on Patentability, Dec. 22, 2010, International Application No. PCT/CA2010/001404.
Written Opinion, Aug. 17, 2011, International Application No. PCT/CA2011/000599.
International Preliminary Report on Patentability, Aug. 17, 2011, International Application No. PCT/CA2011/000599.
Canadian Office Action, Aug. 6, 2012, Canadian Application No. 2750691.
Canadian Office Action, May 8, 2013, Canadian Application No. 2750691.
Canadian Office Action, Nov. 20, 2013, Canadian Application No. 2750691.
Supplementary European Search Report, Sep. 26, 2013, EP Application No. 10755346.3.
First Chinese Office Action, Aug. 13, 2013, CH Application No. 201080022796.0.
Second Chinese Office Action, Jul. 30, 2014, CH Application No. 201080022796.0.
Canadian Office Action, Nov. 4, 2014, Canadian Application No. 2773620.
Supplementary European Search Report, Dec. 11, 2103, EP Application No. 10 81 4843.
Written Opinion, Jun. 26, 2012, International Application No. PCT/CA2012/000277.
International Preliminary Report on Patentability, Jun. 26, 2012, International Application No. PCT/CA2012/000277.
Supplementary European Search Report, Nov. 3, 2014, International Application No. PCT/CA2012/000277.
Supplementary European Search Report, Dec. 20, 2103, EP Application No. 10 81 4843.8.
First Chinese Office Action, Sep. 23, 2013, CH Application No. 201180026189.6.
Second Chinese Office Action, May 7, 2014, CH Application No. 201180026189.6.
Response to First Chinese Office Action, CH Application No. 201180026189.6, Jan. 16, 2014.
Response to Second Chinese Office Action, CH Application No. 201180026189.6, Jul. 30, 2014.
International Search Report, Jun. 26, 2012, International Application No. PCT/CA2012/000277.
Rushton J.D., Sirrine J.E., Collection and Treatment of Odorous Kraft Mill Gases. Paper Trade Journal/ 1972, pp. 36-37. (Dec. 18, 1972).
Fourth Chinese Office Action, Jul. 30, 2013, CH Application No. 200880013191.8.
Response to Third Chinese Office Action, CH Application No. 200880013191.8, Apr. 12, 2013.
Third Chinese Office Action, Apr. 1, 2013, CH Application No. 200880013191.8.
Response to Second Chinese Office Action, CH Application No. 200880013191.8, May 7, 2014.
Second Chinese Office Action, Nov. 27, 2013, CH Application No. 200880013191.8.
Response to First Chinese Office Action, CH Application No. 200880013191.8, Mar. 16, 2010.
First Chinese Office Action, Apr. 16, 2012, CH Application No. 200880013191.8.
Perry et al. Chemical Engineers' Handbook (5th Ed.) McGraw-Hill Book Co. USA;15BN 0-67-049478-9; p. 22-4, 1973.
Notice of Allowance, Dec. 31, 2014, U.S. Appl. No. 13/699,752.
Notice of Allowance, Jan. 21, 2015, U.S. Appl. No. 13/394,828.
Canadian Office Action, Mar. 23, 2009, Canadian Patent Application No. 2532640.
Canadian Office Action, Aug. 5, 2008, Canadian Patent Application No. 2532640.

\* cited by examiner

EROSION-RESISTANT CONDUCTIVE COMPOSITE MATERIAL COLLECTING ELECTRODE FOR WESP

CROSS-REFERENCE TO RELATED APPLICATION

This application claims the benefit of U.S. Provisional Application No. 61/468,199 to McGrath filed on Mar. 28, 2011, entitled "EROSION-RESISTANT CONDUCTIVE COMPOSITE MATERIAL COLLECTING ELECTRODE FOR WESP", the entire content of which is incorporated herein by reference.

FIELD OF THE INVENTION

The present invention is concerned with conductive composite material for wet electrostatic precipitator (WESP) applications.

BACKGROUND TO THE INVENTION

Wet electrostatic precipitators have been used for many years to remove dust, acid mist and other particulates from water-saturated air and other gases by electrostatic means. In a WESP, particulates and/or mist laden water-saturated air flows in a region of the precipitator between discharge and collecting electrodes, where the particulates and/or mist are electrically charged by corona emitted from high voltage discharge electrodes. As the water-saturated gas flows further within the WESP, the charged particulate matter and/or mist is electrostatically attracted to grounded collecting plates or electrodes where it is collected. The accumulated materials are continuously washed off by both an irrigating film of water and periodic flushing.

WESPs are used to remove pollutants from gas streams exhausting from various industrial sources, such as incinerators, wood products manufacturing, coke ovens, glass furnaces, non-ferrous metallurgical plants, coal-fired electricity generation plants, forest product facilities, food drying plants and petrochemical plants.

Traditionally, the collecting surfaces and other parts of electrostatic precipitators exposed to the process gas stream have been fabricated from carbon steel, stainless steel, corrosion and temperature resistant alloys and lead. However, such materials tend to corrode and/or degrade over time especially when the precipitators are used in severe environments. Carbon and stainless steel tend to corrode or erode under severe acid conditions. Reinforced thermoplastics tend to erode and/or delaminate due to severe corrosive conditions and localized high temperature in regions of sparking.

Other methods have been used to fabricate collecting surfaces involving the use of plastic materials; however, these materials rely on a continuous water film to ensure electrical grounding of the equipment, which has proved to be a problem. PVC, polypropylene and other similar materials have been used but have suffered from holes and flashover-induced fires and, therefore, are not widely used.

In PCT publications Nos. WO2008/154,735 and WO2010/108,256, assigned to the assignee hereof and incorporated herein by reference, there is described electrically-conductive, corrosion resistant and temperature and spark resistant composite material with good heat dissipation for use in the fabricating components used in WESPs. Such materials generally comprise carbon fiber with a thermosetting resin in a cross-linked structure.

As described therein, the electrically conductive composite material utilized herein is a conductive composite material designed for highly corrosive operating conditions including dry and saturated mist environments with elevated temperatures. The composite material is a blend of carbon fibers and thermosetting resins developed for wet electrostatic precipitation, where such materials are subjected to corona voltage flash over, spark, erosion, corrosion and power arc.

In particular, the composite material comprises carbon fiber within a thermosetting resin where extremely strong molecular building blocks form totally cross-linked structures bonded to each other and at interconnects. The resultant network has proven to withstand high voltage current after the onset of corona in the tubes of the electrostatic precipitator, obtaining voltage flash over without pitting the conductive hybrid composite material. Such spark resistance and arc-over may be generated at a voltage of approximately 60 to 95 KV at up to 500 to 1000 milliamps for a duration of approximately 1 millisecond. The composite material is also resistant to sustained arcing with a duration of up to 4 to 5 seconds. These properties are highly desirable to minimize corrosion and restrict high intensity heat generation and to prevent structural, mechanical or chemical changes to the conductive hybrid composite material.

The carbon fibers woven into a seamless biaxial material sleeve creates a dense network imparting electrical conductivity and thermal dispersion within thermosetting resins.

Strong molecular building blocks form totally cross-linked structures bonded to each other and as interconnects, producing a three-dimensional network, stitched through the thickness of the laminate. The carbon fibers are woven into seamless biaxial and triaxial material. This arrangement imparts excellent electrical conductivity and superior thermal dispersion through the laminate.

In addition to the electro-conductive characteristics and excellent corrosion resistant properties, the conductive hybrid composite material also provides further advantages as a material of construction, reducing the dead load weight by one half or more, due to the lightweight and high strength qualities of carbon fiber which results in economic benefits before installation especially beneficial for tube bundles made from stainless steel and even higher grades of titanium.

The composite may be prepared by weaving, stitching, alignment through vibration using frequency while the material may be formed into shapes that are tubes and sheets by prior art processes known as vacuum infusion, pultrusion, filament winding and autoclaving.

The conductive composite material overcomes the problems of corrosion affecting stainless steel, alloys and titanium within a highly corrosive environment, saturated mists and elevated temperatures, by improving on prior art thermosetting resins and carbon fiberglass compositions that cannot withstand the corona voltage flash over and power arcs at up to 100,000 Volts.

SUMMARY OF THE INVENTION

It has now been found that the erosion direction and density on the WESP collecting electrodes prepared from such electrically-conductive, corrosion resistant and temperature and spark resistant material can be controlled by controlling the weave pattern of the carbon fibers and fabric thickness. In this regard, a tighter weave creates a greater density of erosion lines in the collecting electrode while thicker carbon fiber fabrics create erosion lines with fewer turns and branching.

Accordingly, in one aspect of the present invention, there is provided a collecting electrode comprises of an electrically-conductive, corrosion resistant and temperature and spark resistant composite material comprising carbon fiber in a cross-linked thermosetting resin, wherein erosion direction and density on the electrode is controlled.

The control of the erosion density and direction may be effected by controlling the weave pattern and/or fabric thickness of the carbon fibers. The carbon fibers preferably are woven in a 2×2 twill arrangement, but other weave patterns may be used, such as 4×4 twill, plain weave and satin weave, may be used.

DESCRIPTION OF PREFERRED EMBODIMENT

Figure 1:
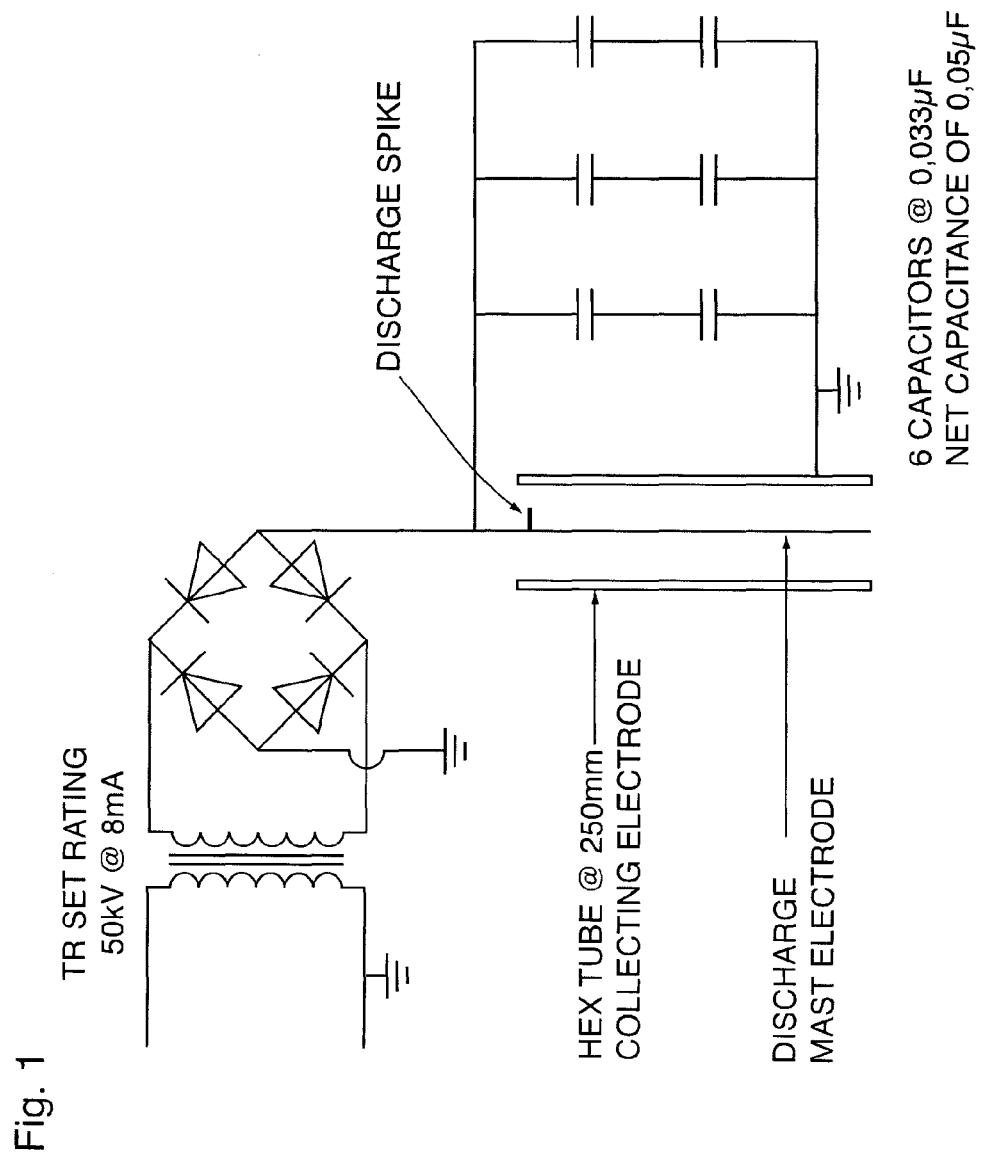
FIG. 1 is a schematic of power-arc testing rig used to evaluate samples for power-arc resistance.

Referring to FIG. 1, a single 3 m long 250 mm hexagonal collecting tube was set up on a laboratory test stand, powered by a 50 kV, 8 mA NWL transformer/rectifier (T/R) set.

A capacitor bank was installed in parallel with the hexagonal tube. The capacitance was equivalent to approximately 277 tubes, each 5 m long and 250 mm equivalent diameter. A pointed discharge spike was installed on the mast (emitting) electrode, adjacent to which composite samples were mounted on the test collecting tube. Power arcs generated approximately 67 Joules to be dissipated at the point of arc contact on the sample. The controller on the T/R set was such that arcs could be counted. These power arcs were robust in nature and sufficiently loud that the integrated arc count reading on the controller could be verified using a stopwatch and manual spark count.

EXAMPLES

Example 1

This Example describes the test results obtained for 304L stainless steel (SS304L).

A sample constructed of SS304L was tested in the test rig of FIG. 1 for comparison purposes. It was found that 3400 arcs caused pitting, 10000 arcs caused severe pitting and metal damage, and 13000 arcs resulted in extensive metal damage. The damage at 10000 arcs was quite significant. This level of arcing is not normally experienced in full scale WESP operation. This level was arbitrarily used as the standard for further arc resistance comparative testing.

Example 2

This Example shows the effect of fiber weave pattern and fabric thickness on erosion density and direction.

Four samples of composite materials were formed into collecting electrodes and arranged in the power-arc testing rig illustrated in FIG. 1. Two of the samples were made from woven 2×2 twill carbon fibre with a high heat distortion temperature, corrosion resistant, epoxy vinyl ester resin (Sample 1 and Sample 2). An additional two samples (Sample B1-A and B1-B) were identically constructed from 1×4 twill carbon fibre fabric and subjected to 3000 and 13000 arcs. After arc testing, the samples were anlayzed under an optical microscope to further understand the mechanism providing the carbon composite laminates with their high level of arc endurance.

Figure 2:
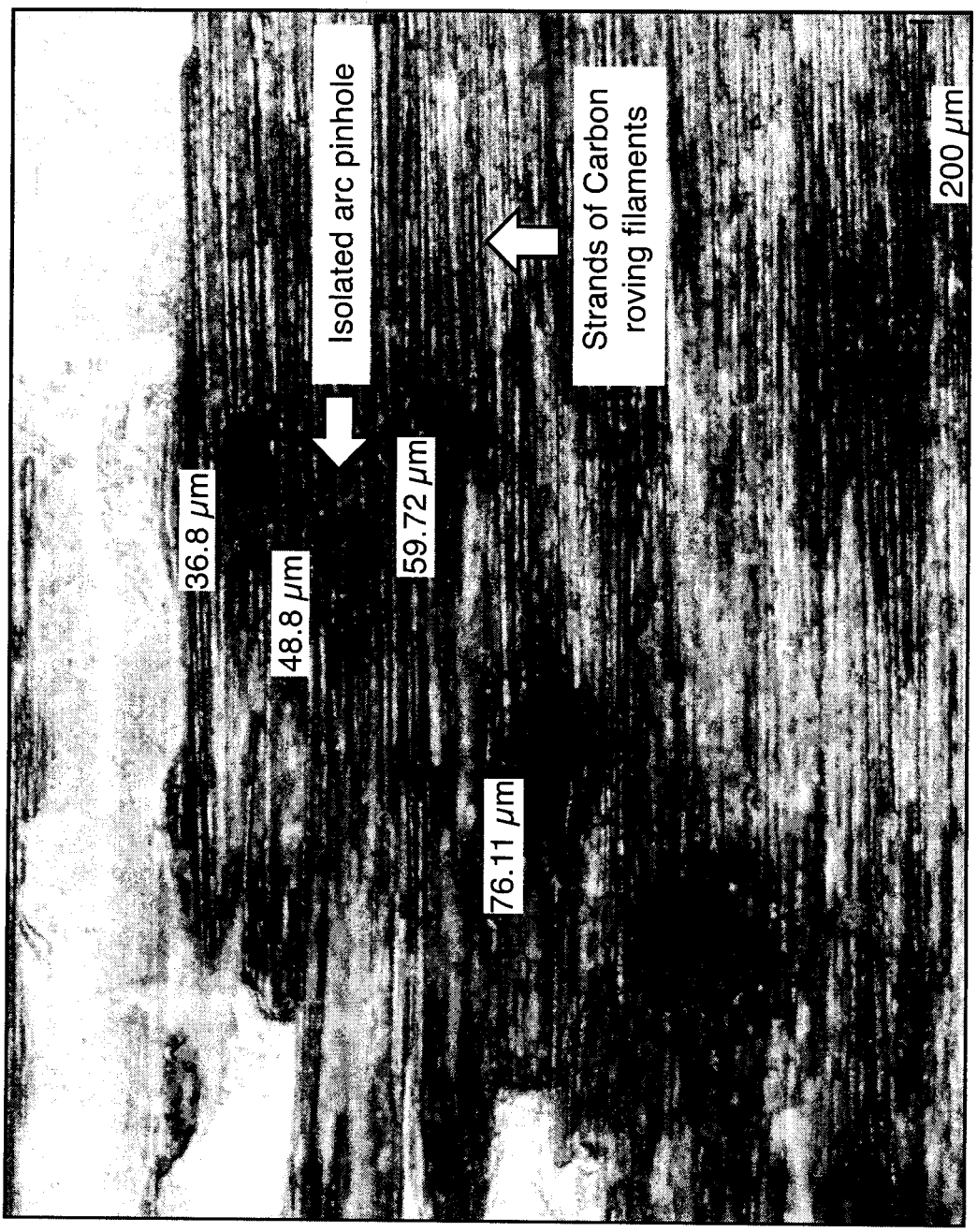
FIGS. 2 to 6 are photographs taken with an optical microscope of samples tested as described in the Examples below.
Figure 3:
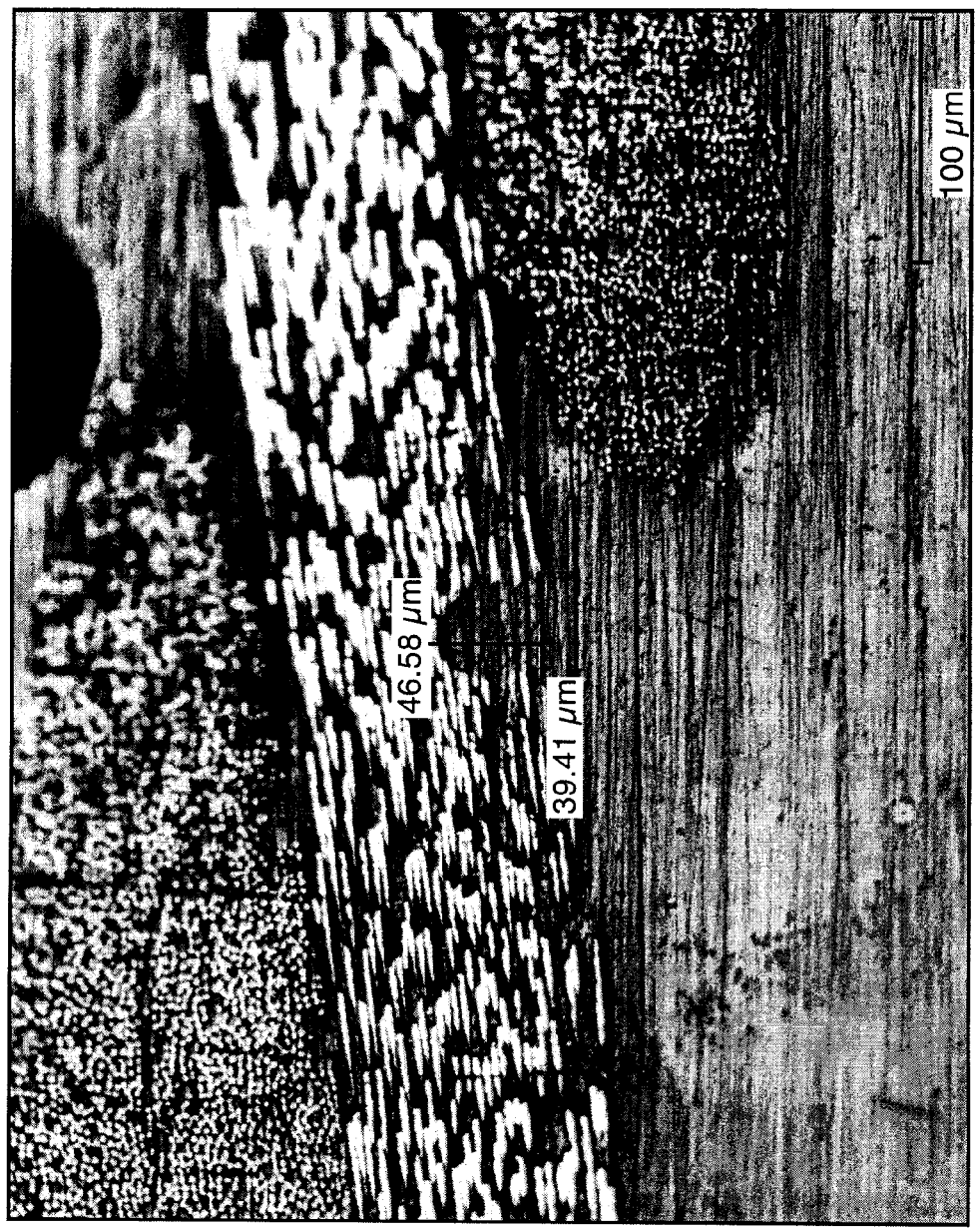

Overall, the total amount of electrical arc erosion in all of the samples was relatively small compared to the total surface area tested and the thickness of the laminate. FIG. 2 shows a top view and FIG. 3 a cross sectional view of a typical arc pinhole that were found at the perimeter of the testing areas. Crude surface erosion area estimate was performed on Sample 1 giving 200 to 1400 arcs per $mm^2$ of surface erosion. The amount of arc erosion in Sample 1 was comparatively close to Sample B1-A with 3000 arcs.

Figure 5:
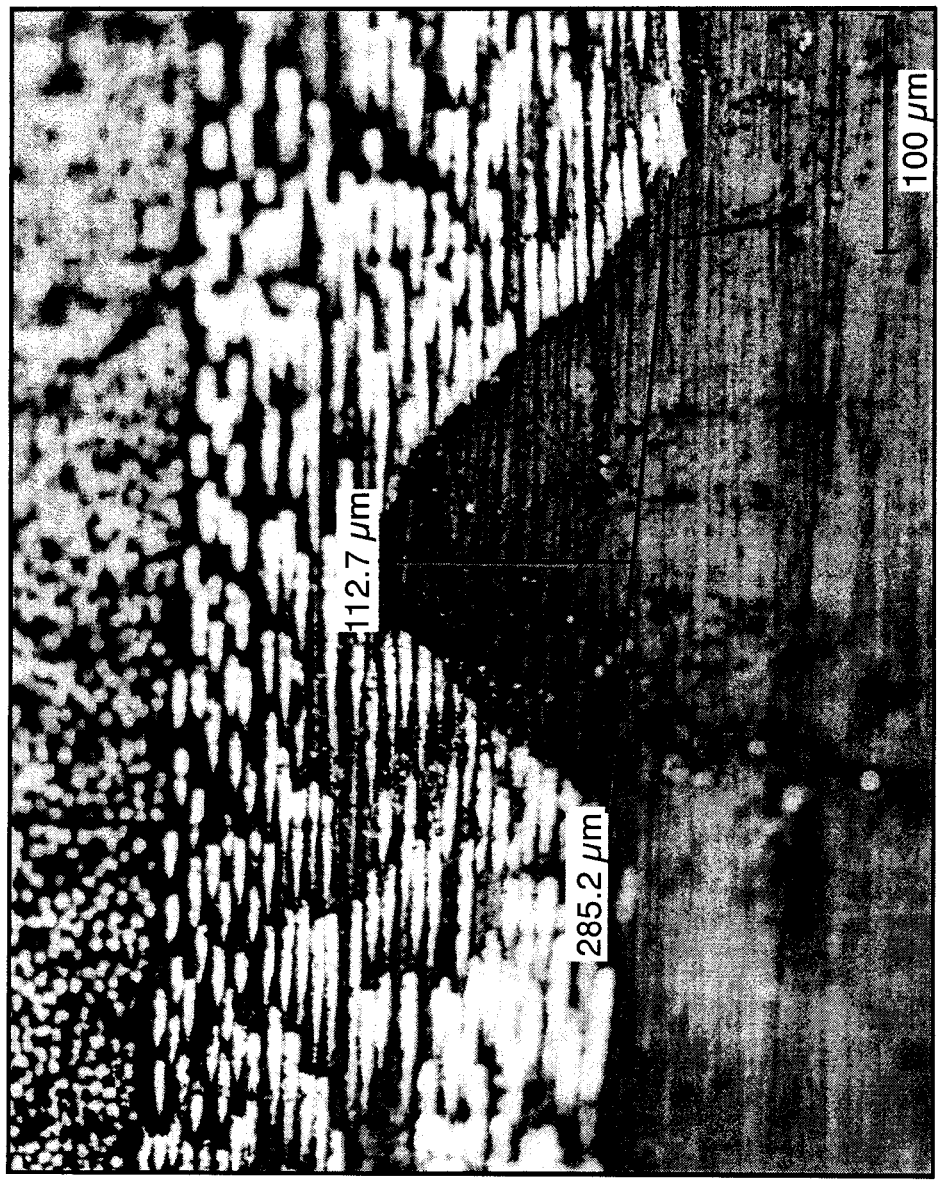
Figure 6:

In Sample 1, the cross section of the erosion running in bundle of transverse direction of the fibers was found to be well defined "V" (FIG. 5) with a depth of the observed burns ranging from 46 to 113 μm with an opening of 39 to 285 μm. The maximum erosion depth observed was relatively small, with only 3.9% of the laminate thickness and 15.6% of the surface lamina thickness eroded. The cross section of the erosion running in longitudinal direction of the tow was found to be less well defined (FIG. 6). The length of the observed burns were around 380 μm with varying depth across its length.

With the addition of more arcs (Sample 1 @2120 arcs vs. Sample 2 @10041 arcs), the majority of the traits previously seen were duplicated; however, the length and width of the erosion increased and the maximum observed cross sectional depth of an erosion increased to 364.2 μm. This translates to 11% of the laminate and ⅔ of the surface lamina.

Figure 4:
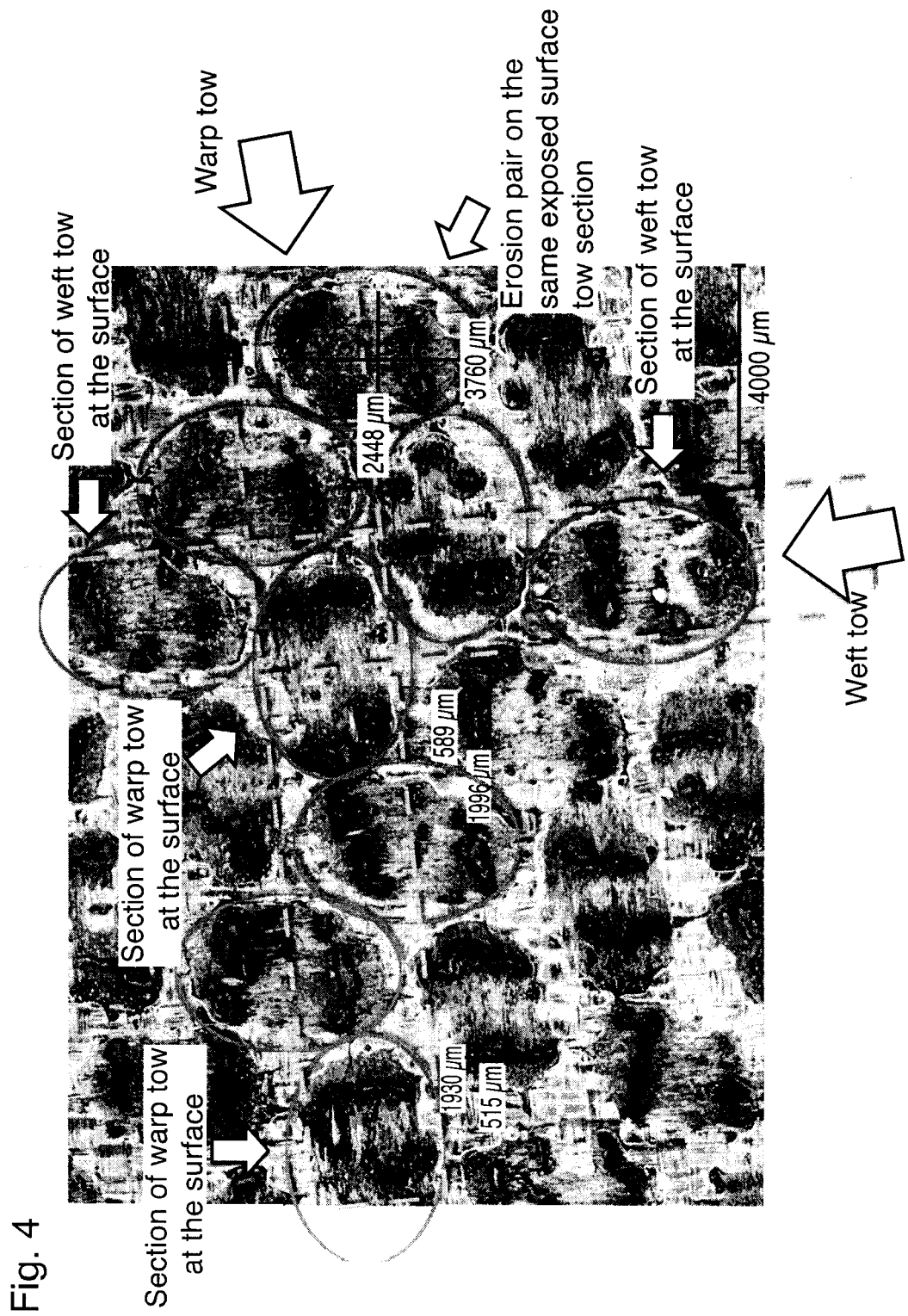

With Samples 1 and 2, the agglomeration of arc erosion formed straight lines running transversely to the targeted surface tow (see FIG. 4). The erosion in the 2×2 twill samples had a tendency to erode in two parallel lines (pairs of lines circled in FIG. 4. Each of these erosion lines were associated with a corresponding tow in the layer beneath. In FIG. 4, dotted lines were drawn following both edges of a single tow in the weft and a single tow in the warp direction. Following these tows it was possible to see how the cycling of two up and two down twill pattern controls the direction of the erosion lines.

Sample 2, with 10041 arcs, had an additional trend from those seen in Sample 1, with 2120 arcs (see FIG. 4). Once the erosion depth reached tows beneath which are running in the opposite fabric direction, the path of the erosion changed to be transverse to that of the newly targeted tow. This created right angle turns and branches in the erosion lines running in either the warp or weft directions.

As for the 1×4 Twill samples, the difference between the arc erosion of Samples B1-A and B1-B (1×4 Twill) and the previously discussed Samples 1 and 2 (2×2 Twill) was the location of the main erosion concentrations. Sample B1-A and B1-B erosion was focused mainly on the tows of the fabric running in the Twill-1 direction and the Twill-4 direction was relatively clear of any major erosion. In contrast to this Sample 1 (2×2 Twill), arc erosion were evenly distributed on both the warp and the weft directions.

The above findings provide the possibility of controlling the erosion density and direction by controlling the fabric weave pattern and the fabric thickness. As seen in Sample 2, each crossover point in the weave contained one erosion line. Hence it can be concluded that a tighter weave creates a greater density of erosion lines. Thicker fabrics will also create erosion lines with fewer turns and branching.

After arc testing of Sample 2 (10041 arcs) the only observation to the naked eye was surface discoloration caused by the sample's loss of luster, or sheen. Since the damage was so small, it was concluded that the new conductive composite has better resistance to arc erosion than SS304L.

Example 3

This Example shows the arc performance of joints between WESP components.

In the assembly of a WESP from composite carbon fibre materials, components are adhered together using a bonding formulation. The assembly of such WESPs is described in PCT publication No. WO 2011/029186, assigned to the assignee hereof and the disclosure of which is incorporated herein by reference. Formulations for use as the adhesive are described in PCT publication No. WO 2011/147016, assigned to the assignee hereof and the disclosure of which is incorporated herein by reference.

The adhesive bonding of sub components is a major aspect in the assembly of the new WESP design. To evaluate arc performance of the joint, two sample plaques were bonded together using a conductive bonding formulation. One sample had a joint line as thin as possible (<0.25 mm) and another had a thick joint line (approximately 1.25 mm).

Two corrosion resistant conductive bonding formulations were tested, one variant with a blend of conductive carbon fibers and another with a carbon nanotubes/conductive carbon fiber blend, which was formulated to the same material cost point as the first.

Prior to applying the bonding formulation, the substrate plaques were sanded to remove insulative surface resin. The sanding stopped once 80% of the surface showed anisotropic reflection caused by the exposure of the carbon fibers. The conductivity of the surface was tested in multiple locations to confirm that the majority of the insulative resin was removed.

The joints were subjected to 10000 power arcs in the test facility at an electrical condition approximating the full-scale application. Visual observations showed similar arc erosion to the non-bonded laminates, discussed above.

SUMMARY OF THE INVENTION

In summary of this disclosure, electrically-conductive, corrosion resistant and temperature and spark resistant composite materials comprising carbon fibre and thermosetting cross-linked resin have improved arc resistance in terms of erosion density and direction by controlling the weave pattern and fabric thickness. Modifications are possible within the scope of this invention.

What I claim is:

1. A collecting electrode for a wet electrostatic precipitator fabricated from an electrically-conductive, corrosion resistant and temperature and spark resistant composite material, the composite material comprising a generally evenly woven carbon fiber within a thermosetting resin in a cross-linked structure, wherein erosion direction and density on the electrode is controlled by varying the weave pattern of the carbon fibers and fabric thickness of the carbon fibers.

2. The collecting electrode claimed in claim 1, wherein the carbon fibers are woven in a 2×2 twill arrangement.

3. The collecting electrode claimed in claim 1, wherein increasing the tightness of the weave pattern of the carbon fibers increases the density on the electrode.

4. The collecting electrode claimed in claim 1 wherein increasing the thickness of the carbon fibers creates erosion lines with fewer turns and branching.

* * * * *